United States Patent
Wesselink et al.

(10) Patent No.: US 7,215,998 B2
(45) Date of Patent: May 8, 2007

(54) SYNCHRONOUS PACEMAKER WITH AV INTERVAL OPTIMIZATION

(75) Inventors: Willem Wesselink, Doesburg (NL); Geeske Van Oort, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 258 days.

(21) Appl. No.: 10/751,365

(22) Filed: Jan. 5, 2004

(65) Prior Publication Data

US 2005/0043764 A1    Feb. 24, 2005

(51) Int. Cl.
*A61N 1/08*    (2006.01)

(52) U.S. Cl. .......................................... 607/25; 607/17

(58) Field of Classification Search .................. 607/17, 607/25

See application file for complete search history.

(56) References Cited

U.S. PATENT DOCUMENTS

| | | | |
|---|---|---|---|
| 4,303,075 A | 12/1981 | Heilman et al. | 607/4 |
| 4,316,472 A | 2/1982 | Mirowski | 607/9 |
| 4,375,817 A | 3/1983 | Engle et al. | 607/4 |
| 4,379,459 A | 4/1983 | Stein | 607/9 |
| 4,384,585 A | 5/1983 | Zipes | 607/5 |
| 4,527,568 A | 7/1985 | Rickards | 607/25 |
| 4,566,063 A | 1/1986 | Zolnowsky | 712/241 |
| 4,587,970 A | 5/1986 | Holley et al. | 607/15 |
| 4,726,380 A | 2/1988 | Vollmann et al. | 607/15 |
| 4,727,877 A | 3/1988 | Kallok | 607/5 |
| 4,800,883 A | 1/1989 | Winstrom | 607/7 |
| 4,830,006 A | 5/1989 | Haluska et al. | 607/4 |
| 4,880,005 A | 11/1989 | Pless et al. | 607/15 |
| 4,920,965 A | 5/1990 | Funke et al. | 607/9 |
| 4,949,719 A | 8/1990 | Pless et al. | 607/7 |
| 4,953,551 A | 9/1990 | Mehra | 607/5 |
| 5,099,838 A | 3/1992 | Bardy | 607/2 |
| 5,117,824 A | 6/1992 | Keimel et al. | 607/4 |
| 5,131,388 A | 7/1992 | Pless et al. | 607/5 |
| 5,144,949 A | 9/1992 | Olson | 607/17 |
| 5,158,078 A | 10/1992 | Bennett et al. | 607/27 |
| 5,163,427 A | 11/1992 | Keimel | 607/5 |
| 5,188,105 A | 2/1993 | Keimel | 607/5 |
| 5,199,428 A | 4/1993 | Obel et al. | 607/44 |
| 5,207,218 A | 5/1993 | Carpentier et al. | 607/36 |
| 5,269,298 A | 12/1993 | Adams et al. | 607/5 |
| 5,311,388 A | 5/1994 | McLaren | 242/343 |
| 5,312,453 A | 5/1994 | Shelton et al. | 607/19 |
| 5,314,430 A | 5/1994 | Bardy | 607/5 |
| 5,330,507 A | 7/1994 | Schwartz | 607/14 |

(Continued)

*Primary Examiner*—Robert E. Pezzuto
*Assistant Examiner*—Tammie K. Heller
(74) *Attorney, Agent, or Firm*—Daniel G. Chapik; Paul H. McDowall; Girma Wolde-Michael

(57) ABSTRACT

A system and method for use in an implanted cardiac pacing device, whereby an optimal AV delay is determined at or near lower rate (pacing) limit (LRL) by determining measuring the variance, or instability, of the QT interval for a set of intervals. In one embodiment, asynchronous "LRL pacing" with a first programmed AV delay determines a measure of QT variance. The difference between the maximum QT and the minimum QT is expressed as QT difference (QTD). For each programmed AV delay the QT variance is again measured and the optimal AV delay produces minimum QTD. In another embodiment, AV delay is modulated around base values for a time. The difference between QT for the modulated AV and for the base AV (dQT) is measured at each base value, and the optimal AV delay corresponds to the smallest dQT.

22 Claims, 10 Drawing Sheets

U.S. PATENT DOCUMENTS

| | | | |
|---|---|---|---|
| 5,330,511 A * | 7/1994 | Boute | 607/25 |
| 5,331,966 A | 7/1994 | Bennett et al. | 600/508 |
| 5,354,316 A | 10/1994 | Keimel | 607/15 |
| 5,534,016 A | 7/1996 | Boute | 607/9 |
| 5,545,186 A | 8/1996 | Olson et al. | 607/14 |
| 5,560,368 A | 10/1996 | Berger | 600/517 |
| 5,713,930 A | 2/1998 | Van Der Veen et al. | 607/25 |
| 5,800,465 A | 9/1998 | Thompson | 607/9 |
| 6,456,880 B1 * | 9/2002 | Park et al. | 607/25 |

* cited by examiner

SYNCHRONOUS PACEMAKER WITH AV INTERVAL OPTIMIZATION

FIELD OF THE INVENTION

The present invention relates to medical devices and, more particularly, to a subsystem and method for implantable pacemakers having a synchronous mode and the capability of adjusting AV delay interval.

BACKGROUND OF THE INVENTION

The advantages of dual chamber synchronous pacing are well recognized in the art. Pacemakers that can operate in one or more synchronous modes are able to take advantage of the heart's natural atrial, or sinus-activated, depolarizations. This allows the atrium to control the ventricular response rate where appropriate, and offers the improvement in ejection fraction that results from synchronizing the ventricular pacing stimulation with the atrial contraction. Prior studies have shown that the improvement in ventricular output due to synchronous pacing is most pronounced at relatively low heart rates. At higher heart rates the increase in cardiac output is largely due to the increased rate of contractions, but at lower rates there is a significant increase in efficiency that results from synchronous action. Accordingly, while the AV interval can be controlled to vary with rate, the most important value of the AV=f(r) curve is the lower rate limit (LRL). Available modes of pacing that provide synchronous pacing include VDI, VDD, DVI, DDD and DDD as well as rate-responsive variations thereof, among others.

The pacemaker art has also come to include multi-mode designs having the capability to which modes in response to changing patient conditions. Most dual and multi-chamber pacemakers are programmable to distinct modes, or are configured to switch automatically from one mode to another under certain prescribed conditions. See, for example, U.S. Pat. No. 4,527,568 and U.S. Pat. No. 4,920,965. But as a general rule it is advantageous to operate in a synchronized mode as much as possible wherein an atrial sense (AS) or delivered atrial pace pulse (AP) is followed (in the absence of a natural ventricular contraction) by a ventricular pace pulse (VP) that is timed to occur at a predetermined AV interval, or delay following the atrial event.

It is known that it is desirable to optimize the AV delay (AV), and also to set AV as a function of rate. See U.S. Pat. No. 5,330,511, Boute, assigned to the assignee of this invention and incorporated herein by reference in its entirety. The prior art shows a number of examples of pacemakers that attempt to adjust AV as a function of a sensed variable. See U.S. Pat. No. 4,303,075, wherein AV delay is modified in accordance with a sensed measure of stroke volume. U.S. Pat. No. 5,713,930 discloses setting AV delay by monitoring QT interval at different values of AV to determine the AV delay that corresponds to ventricular fusion, and then setting AV to a value just less than that corresponding to fusion. The pacemaker of the above-mentioned Boute patent optimizes AV by monitoring QT interval (QT) at different values of AV while pacing at LRL, and selecting the AV that corresponds to the longest QT. The following Table 1 lists patent references relating to the subject matter of this invention:

TABLE 1

| PATENT NO. | INVENTOR(S) | ISSUE DATE |
|---|---|---|
| U.S. Pat. No. 4,303,075 | Heilman et al. | Dec., 1981 |
| U.S. Pat. No. 5,330,511 | Boute | Jul. 19, 1994 |
| U.S. Pat. No. 5,534,016 | Boute | Jul. 9, 1996 |
| U.S. Pat. No. 5,560,368 | Berger | Oct. 1, 1996 |
| U.S. Pat. No. 5,713,930 | ven der Veen et al | Feb. 3, 1998 |

All patent references listed in Table 1 above are hereby incorporated by reference in their respective entireties. As those of ordinary skill in the art will appreciate upon reading this Summary of Invention, Detailed Description and claims as set forth below, many of the devices and methods disclosed in the references of Table 1 may be modified advantageously by using the teachings of the present invention.

The above-listed U.S. Pat. No. 5,330,511 purports to base AV optimization on examining QT behavior at different AV intervals. This technique involves finding a value of QT at each AV test value, and selecting as optimal the AV that corresponds to the longest QT. See FIG. 6A for a representation of this aspect of the prior art. However, this test depends upon finding a stable QT at each AV test value, and this is difficult in practice. This reference notes that a three-minute waiting period is required after each change to a new AV level in order to let QT stabilize, and that fact alone makes for a lengthy test where up to 12 different AV values are tested. Further, it has been found that the QT interval remains sufficiently unstable even after three minutes to enable finding a value of QT precisely enough to be able to compare the QT values corresponding to different AV test values and determine which one is the maximum QT. Such instability may be the result of slow catecholamine feedback or other mechanisms. Thus, while the optimum value of AV is indeed that where QT is a maximum, in practice this is difficult to measure.

There thus remains a need in the art for a more reliable and precise method for measuring optimum AV interval for use in an implanted cardiac pacing device. There is a need for an improved system and method of periodically determining the optimum relationship between AV interval and pacing rate for a patient at one or more low pacing rates, and for making this determination reliably and in much less time than prior art methods. Also, it is desirable to utilize a parameter such as QT, or another measure of PQRST cardiac-cycle signals to obtain the needed information, so that no extra sensor has to be employed.

BRIEF SUMMARY OF THE INVENTION

The system and methods of the present invention involves monitoring and/or measuring QT interval variability subsequent to a change in a programmed AV interval. Because relatively immediate hemodynamic change(s) occurring as a result of changes to the AV interval, the system and methods are employed to quantitatively and qualitatively optimize the AV interval toward the enhancement of cardiac contractility. Additionally, the inventors have observed that a change in pacing rate (expressed in pace-per-minute or "ppm") or the occurrence of an extra-systole produces changes in cardiac contractility and also alters the T-waves and QT intervals of the PQRST depolarization-repolarization complex. The resulting changes to the T-waves, or to the QT intervals, when detected relatively immediately. A change in AV interval likewise should produce a change in hemodynamics and contractility. The more optimized the AV interval is, the better the hemodynamic response should be. For this reason, QT interval stability following a change in AV is greatest when the AV interval is hemodynamically optimized. Since the contractility change is immediate, the degree of instability, or variability, of the QT interval, can be detected immediately following a programmed change in the AV interval. The QT interval variability will reflect how well adapted the pacer-selected AV interval is to the actual conditions of a patient's heart. The better the adaptation, the less the instability or degree of variance in QT interval, and vice versa. Thus, while the heart does not stabilize quickly enough following a change in AV to enable an accurate determination of QT interval as such for some time, the variability can be determined and determined quickly, and can serve as an indication of the degree of optimization of the AV interval that is being tested. Accordingly, the following objects are achieved by a system and method that are based on quick determinations of QT variability in response to changes in AV.

The present invention also provides an improved method and system for adapting AV interval to one or more optimized values at low pacing rates, i.e., at and near the lower rate limit (LRL). In particular, it is an object of this invention to provide a method and means for finding an optimized value of AV interval (AV delay) at LRL about by performing a test that can be conducted in a relatively short time.

The present invention also provides an improved method for use in an implanted cardiac device for automatically finding an optimized value of AV delay that is based on observations of change in QT interval or some other designated parameter derived from the PQRST complex.

The present invention also provides a method and system for adjusting the relationship between AV delay and heart rate that can be used in an implanted pacemaker and that can be carried out more quickly and with greater reliability than any prior art technique.

In accordance with the foregoing, the present invention is based on monitoring variations in QT interval, or a related measure of ventricular stimulus response, while pacing at or near LRL and at different values of AV interval. When AV interval is optimized according to the present invention, variations in QT are minimized, and such variations, or differences, can be accurately monitored in a relatively short period of time. In one embodiment, a pacing rate is held constant at or about LRL, and AV is set at a predetermined value and held constant for a short period, e.g., about one minute. The difference between the maximum and minimum observed values of QT is determined, representing QT variability. This is repeated for different values of AV, and the AV value that corresponds to the smallest difference in the Q-T interval (QTD) is selected as optimal. In another embodiment, AV delay is set at a base value and then modulated from the base value (e.g., increased by ΔAV and/or decreased by ΔAV) and the differential change in QT (dQT) due to the modulation is monitored. This step is repeated for a plurality of respective base values of AV delay, and the optimal AV delay is chosen as the AV base value corresponding to the smallest value of dQT. In such embodiments it is the QT instability, or variation in QT that is important, and is monitored in order to determine the optimal AV delay. The optimal AV is the one where QT variance is minimum, indicating the best hemodynamic condition.

The present invention presents different methods, each of which can be programmably selected. The tests to determine optimal AV can be performed automatically (e.g., pro-grammed for a specific time, such as nightly), and can be re-programmed or combined depending on results of the tests.

DETAILED DESCRIPTION OF THE INVENTION

Figure 1:
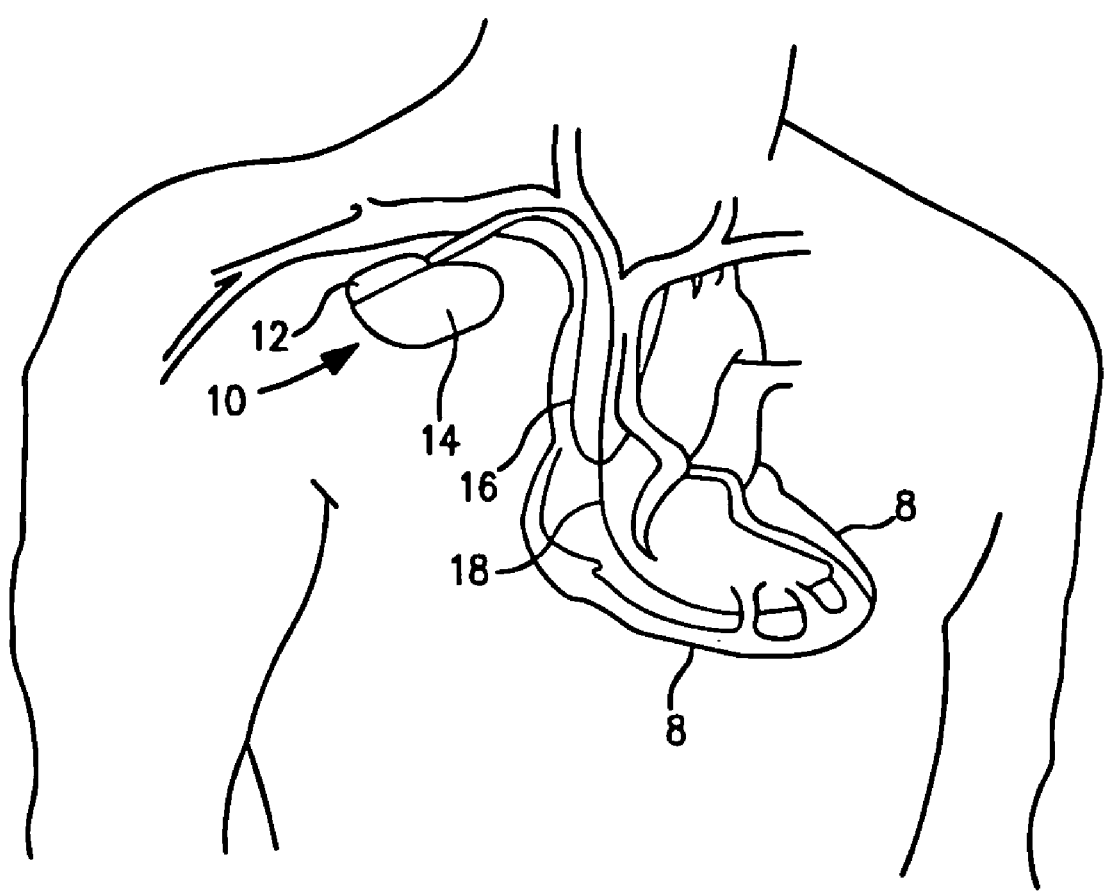
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16,18 attached to hermetically sealed enclosure 14 and implanted near human or mammalian heart 8. Pacing and sensing leads 16,18 sense electrical signals attendant to the depolarization and re-polarization of the heart 8, and further provide pacing pulses for causing depolarization of cardiac tissue in the vicinity of the distal ends thereof. Leads 16,18 may include programmable unipolar or bipolar pace/sense electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
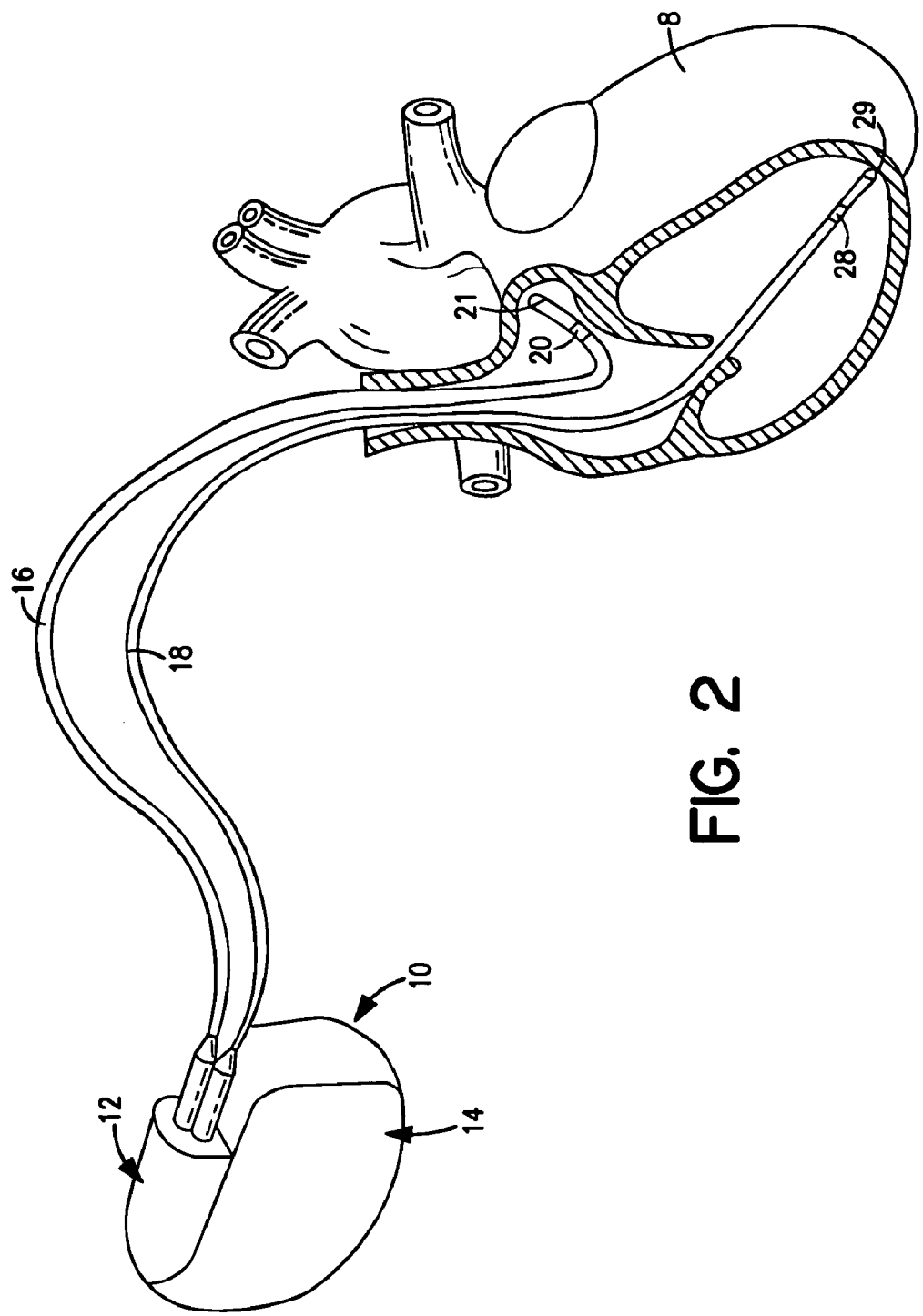
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16,18 extend from connector header module 12 to the right atrium and ventricle, respectively, of heart 8. Atrial electrodes 20,21 disposed at the distal end of atrial pacing lead 16 are located in the right atrium. Ventricular electrodes 28,29 at the distal end of ventricular pacing lead 18 are located in the right ventricle. Of course, while not depicted herein, one or more of the leads 16,18 (or additional leads) may be disposed in operative communication with the left atrium and/or left ventricle. Such embodiments may be used to practice the present invention in the context of cardiac resynchronization therapy (CRT) or other multi-chamber pacing modes.

Figure 3:
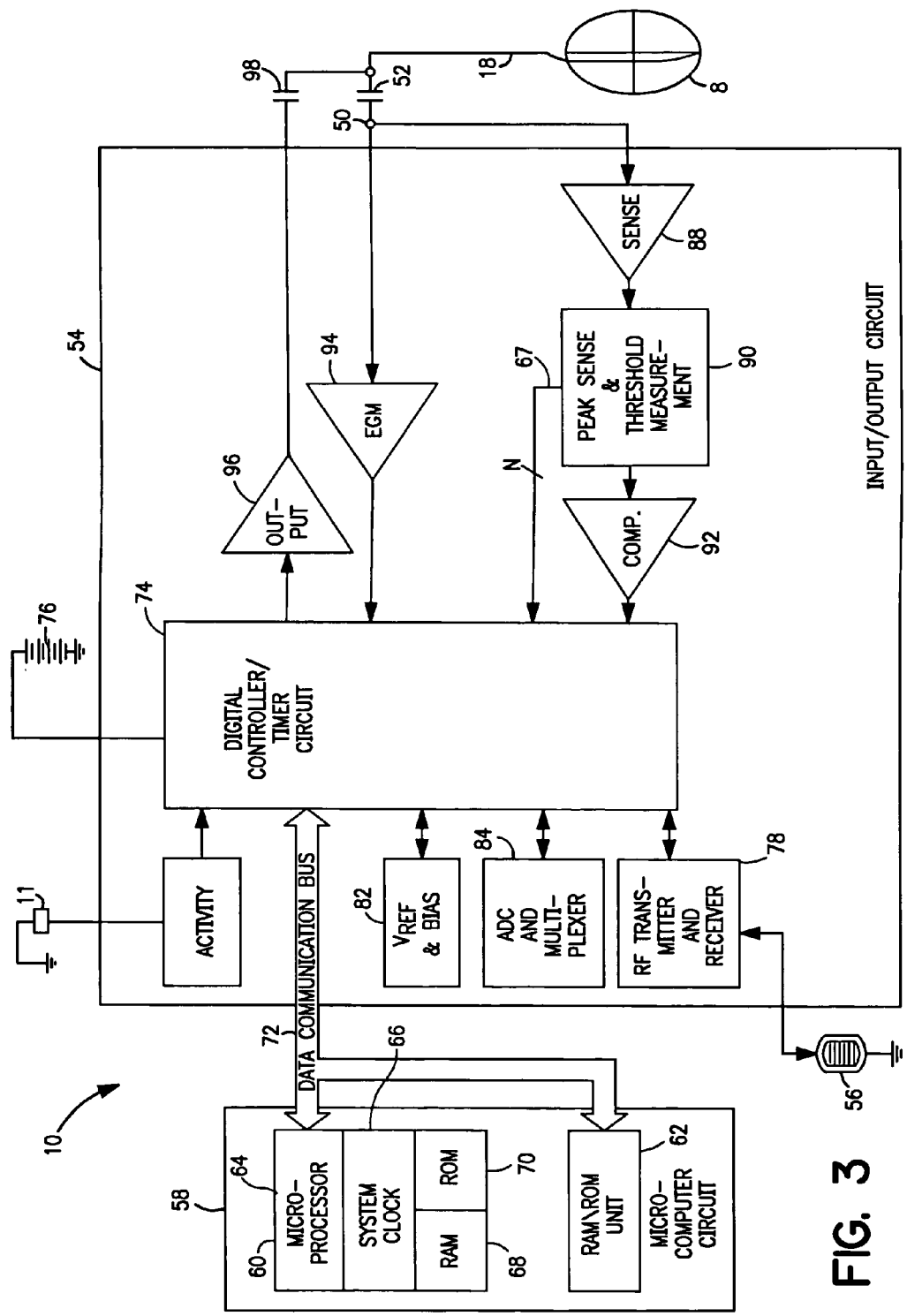
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals (also known as electrogram or "EGM" signals) and battery end-of-life (EOL) or elective replacement intervals (ERI) for battery replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The intracardiac electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention. Accordingly, the methods of the present invention can be advantageously stored on a computer readable medium disposed within the IMD 10.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker cardioverter-defibrillator (PCD)—also commonly referred to as an implantable cardioverter-pacemaker (ICD)—corresponding to any of numerous commercially available such implantable devices. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
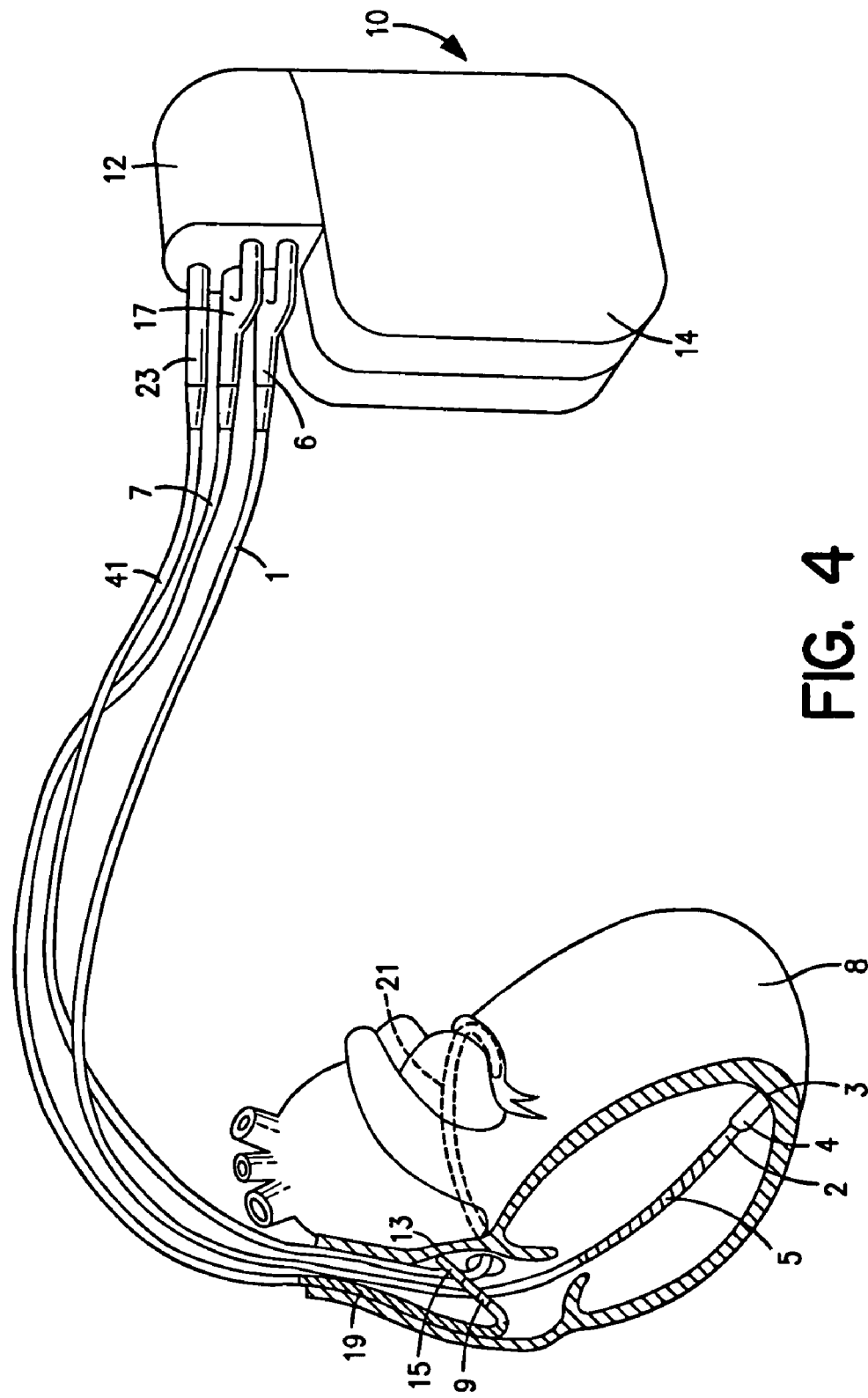
FIG. 4 is a graphic representation of an embodiment of this invention showing an implantable PCD (pacemaker-cardioverter-defibrillator) device interconnected with a heart.
Figure 5:
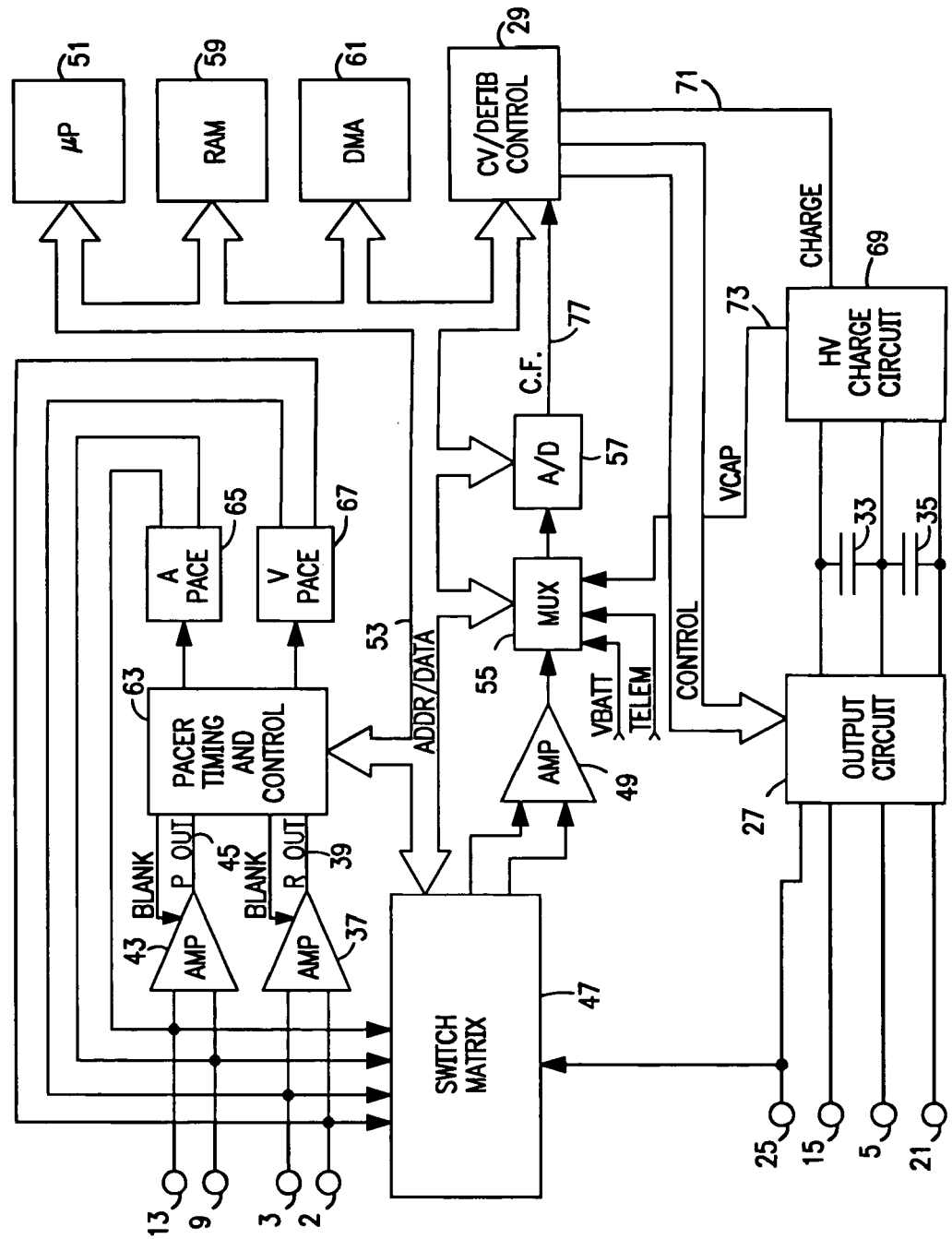
FIG. 5 is a functional schematic diagram of an implantable PCD embodiment of this invention.

FIGS. 4 and 5 illustrate one embodiment of IMD 10 and a corresponding lead set of the present invention, wherein the IMD 10 comprises a so-called triple chamber PCD (or ICD) capable of delivering CRT. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1,7,41 and lead connector assemblies 23,17,6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as only one type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25,15,21,5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33,35) during delivery of defibrillation pulses.

Electrodes 2,3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2,3 exceeds the present sensing threshold.

Electrodes 9,13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9,13 exceeds the present sensing threshold. The general operation of R-wave and P-wave amplifiers 37,43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39,5, and in accordance with the selected mode of pacing on time-out trigger generation of pacing pulses by pacer output circuitry 65,7, which are coupled to electrodes 9,13,2,. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P–R intervals and R–P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33,5 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes adapted to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention thus finds wide application to any form of implantable electrical device for use in conjunction with medical electrical leads.

FIGS. 6B thru 9 illustrate several embodiments of the invention. The methods of determining optimum values of AV delay are generally performed by use of a programmed microprocessor of the form illustrated in FIGS. 3 and 5, but can be embodied in other forms of dedicated circuitry as well.

Figure 6A:
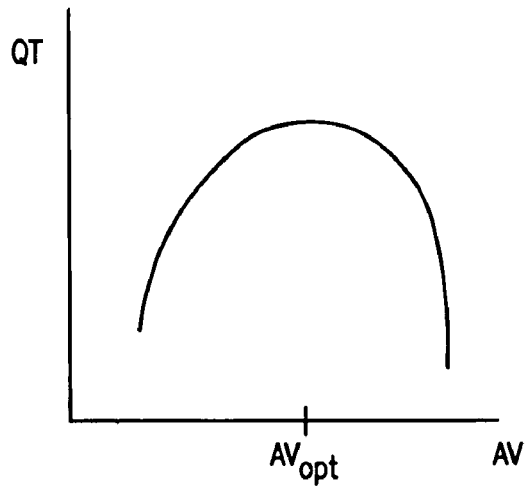
FIG. 6A is a graph depicting the prior art method of determining an optimal value of AV at a given pacing rate.
Figure 6B:
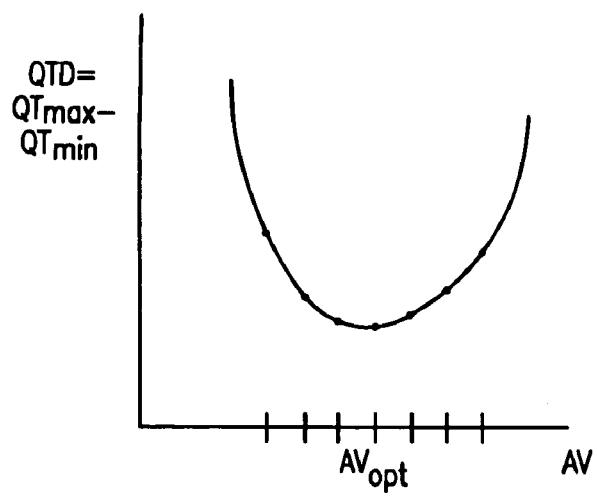
FIG. 6B is a graph depicting a first method embodiment of this invention for determining an optimal value of AV at a given pacing rate.

The graph of FIG. 6B illustrates the data obtained from carrying out a first of the preferred embodiments of the invention. Here, with pacing rate held steady at LRL or another rate near LRL, AV is fixed at a given value for a predetermined duration, either a fixed period of time or a predetermined number of cycles. During the duration, QT is determined each cycle and the maximum and minimum values of QT are determined. Thus, for the duration a QT max and a QT min are obtained, and the difference QT max−QT min is calculated. This difference (QTD) represents variation of QT for the selected value of AV, and is an indicator of how well adapted the AV value is for the rate and the patient's hemodynamics. If the variation is large, AV is not so good; if the variation is small, AV is better. The closer AV is to the optimum value for providing good contractility, the better the QT stability and the smaller the resulting value of QTD. The value of QTD for the duration is stored and then AV is switched to another value, whereupon the test is repeated for another duration. After determining QTD for a range of AV values, the data as indicated in FIG. 6B is available, and the minimum QTD can be determined. The pacemaker takes the value of AV corresponding to the minimum QTD and uses that as the working AV at LRL. As discussed below, the test can be repeated at different pacing rates, if desired, to obtain more data points for a curve representing AV (r), i.e., a curve representing AV as a function of rate. However, as discussed above, adaptation of AV is most useful at lower rates, and one test at LRL may be sufficient.

Figure 6C:
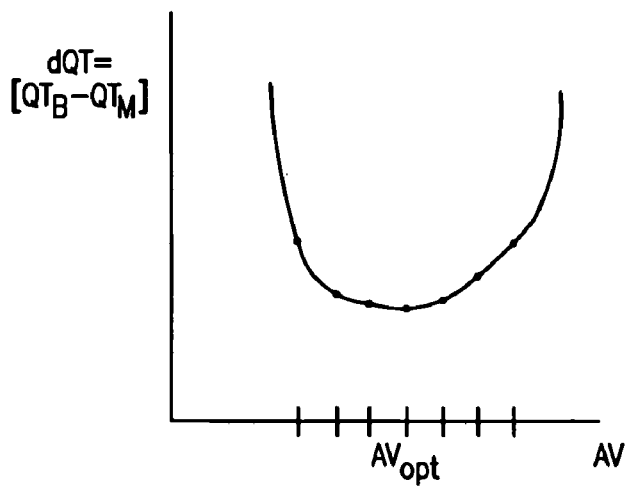
FIG. 6C is a graph depicting a second method embodiment of this invention for determining an optimal value of AV at a given pacing rate.

FIG. 6C illustrates another preferred method of obtaining an optimal value of AV in accord with the invention. In this method, QT variation is determined by fixing a base value of AV, and then modulating AV plus and minus around the base value to see how much variation of QT (dQT) results. Here, a first base value of AV is set, and for a predetermined duration synchronous pacing is carried out with an AV value that equals the base value plus a small modulation from the base. For example, AV can be modulated by first pacing at the base value of AV (AVbase); then adding an increment $\Delta AV$ and pacing at AVbase+$\Delta AV$; then pacing again at AVbase; then subtracting an increment $\Delta AV$, etc., for the duration. For each paced cycle, QT is determined and the difference (dQT) between QT at AVbase and QT when modulated is determined. Then AVbase is changed, AV is again modulated, dQT is determined for the current AVbase, and this is repeated for all desired values of AVbase. As illustrated in the graph of FIG. 6C, the optimum value of AV corresponds to the minimum dQT, indicating best QT stability (minimum QT instability). Examples of modulation that can be used in this embodiment are as follows:

(a) Pace at LRL, with AV=AVbase (n beats), AVbase+$\Delta AV$ (n beats), AVbase (n beats), AVbase−$\Delta AV$, AVbase (n beats), etc., where n and AV are programmable;

(b) Pace at LRL, with AV=AVbase (n beats), AVbase+$\Delta AV$ (n beats), AVbase+2$\Delta AV$ (n beats), AVbase+$\Delta AV$ (n beats), AVbase (n beats), AVbase−$\Delta AV$ (n beats), AVbase−2$\Delta AV$ (n beats), AVbase−$\Delta AV$ (n beats), AVbase (n beats), etc.

Preferably dQt is determined as the largest difference found at any modulation value during a given modulation. For example, if the modulation scheme includes AVbase+ ΔAV and −ΔAV, dQT may be taken as the larger of the differences found at the two modulation points; alternately, it can be the average of those differences. If there is more than one cycle at each modulation value of AV, the average dQT of the n beats can be calculated. Of course, other techniques of determining variance of QT in response to modulation can be used within the practice of this invention.

In the above examples, the value of n may be, for example, 1–5; the value of ΔAV may be in the range of 5–20% of the base value of AV. The test may include doing one of the above sequences just once for each AVbase, or plural times. Further, the sequence may start with the first AVbase set at the current AV value (AVc) and if dQT is found to be smaller than a predetermined amount, then the test may be stopped under the assumption that AV is already optimised.

Figure 7A:
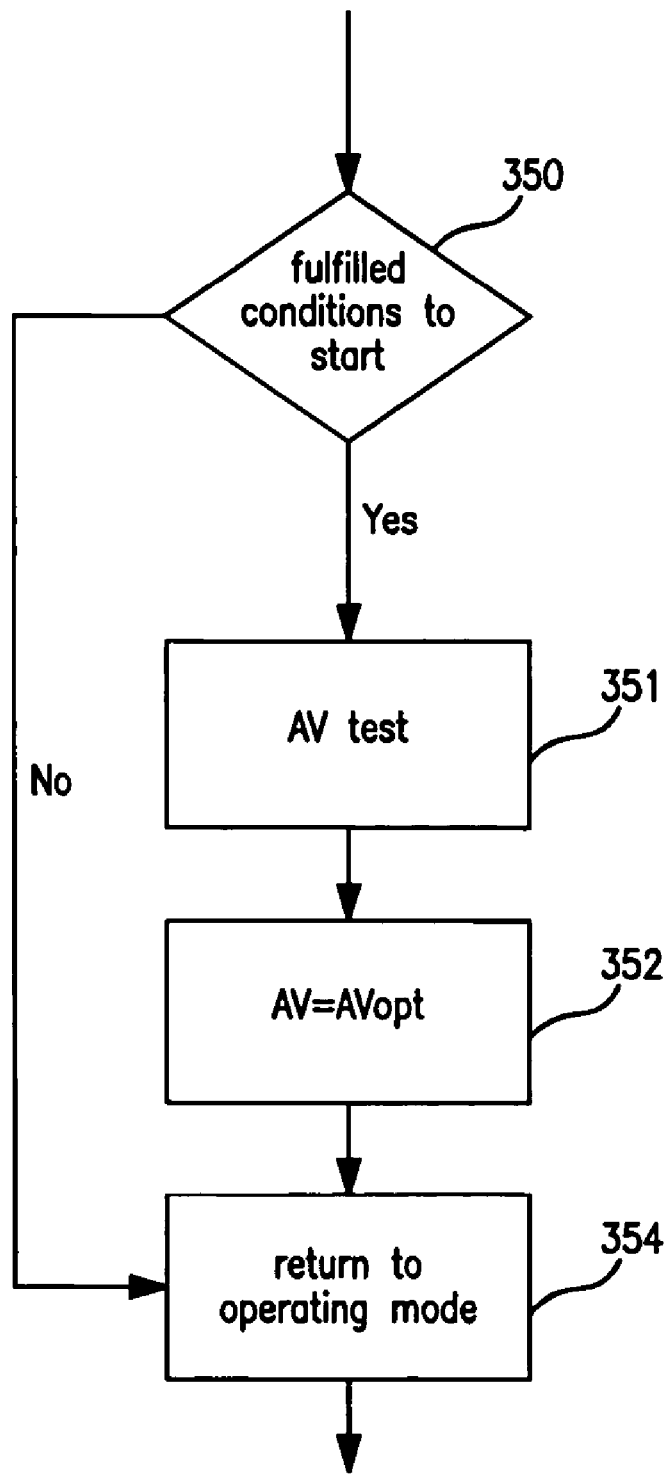
FIG. 7A is an overall flow diagram showing the primary steps taken in accord with this invention for carrying out an AV test and changing AV to a more optimal value.

FIG. 7A illustrates the primary steps for carrying out an AV optimization in accord with this invention. The pacemaker, or other implanted device, may be programmed to test for optimal AV on a timed basis, e.g., hourly or daily. In one preferred embodiment the test is automatically started at night when pacing is expected to be at or near lower rate limit (LRL) in any event. Time to test is determined at step 350 where the device also checks to see if other required conditions are fulfilled. The device is placed in an acceptable synchronous pacing mode (e.g.,DDD) for pacing at LRL. QT stability is checked, suitably over about 3 minutes. While the test to be performed will obtain measures of QT variability, the test cannot be conducted if there is gross instability. The important point in this regard is that there should be no increasing or decreasing trend in QT. Further, consecutive QT values should be within a predetermined bandwidth. It is important to have relative stability in order that the test can determine the influence of AV changes and not be influenced by other factors. Any standard measure of instability can be used, such as measuring the percentage of QT values that differ from the average by more than a predetermined variance. If the conditions are met, the test is carried out as shown at 351. The value of AV at LRL is set as AV=AVopt at 352, and at 354 the device returns to the desired operating mode.

Figure 7B:
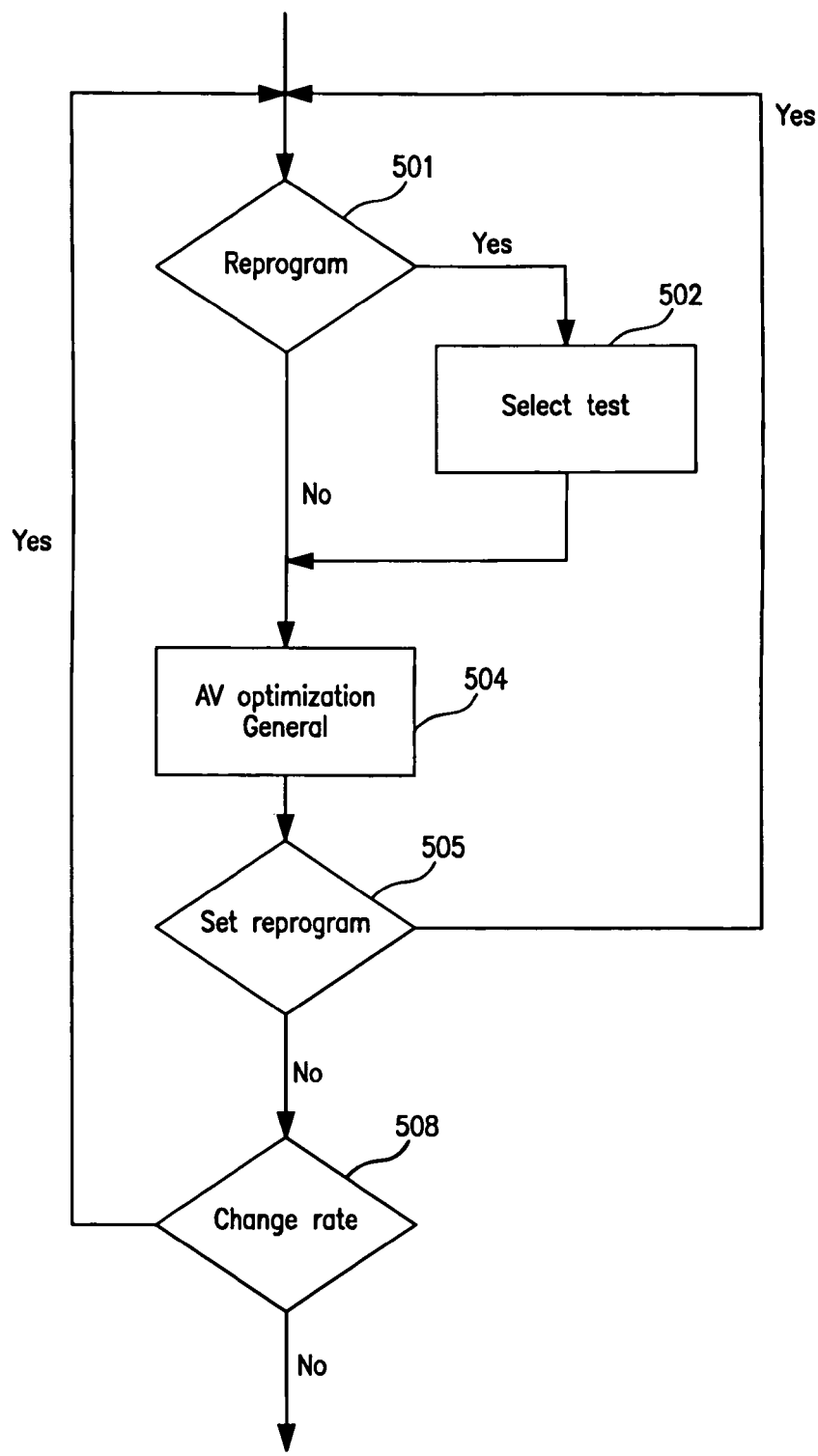
FIG. 7B is another flow diagram showing steps of re-programming the AV test and automatically repeating the test under certain conditions.

FIG. 7B is another flow diagram that illustrates the circumstances where the test is changed to a selected one of a plurality of programmable variations. In this embodiment, when the test is entered at 501 it is determined whether the "reprogram" flag is set. The flag could be set by external programming or by an internally generated decision. If the reprogram flag is set, this means that the test is to be changed, and a different variation is selected at 502. For example, the selection may be that of changing from the embodiment of FIG. 8 to that of FIG. 9; it may embody changing the pattern of modulation in the test of FIG. 9; or it may embody changing the sequence of stepping to different values of AV, as is discussed in more detail below. At 504 the AV optimization test is performed, as illustrated in FIG. 7A. At 505 the device checks to see if the test should be reprogrammed again. This choice may depend, for example, on whether the results of the test that has just been performed are significant, i.e., whether the determined optimal value of AV has a QTD or dQT that is significantly different from that of the current AV (AVc). If the choice at 505 is to reprogram, the algorithm loops back to 501 after a wait. If NO, then at 508 the option is presented of doing another test at a different pacing rate. This option gives the user the choice of measuring QTopt at several low rates in order to construct an AV(r) curve.

Figure 8:
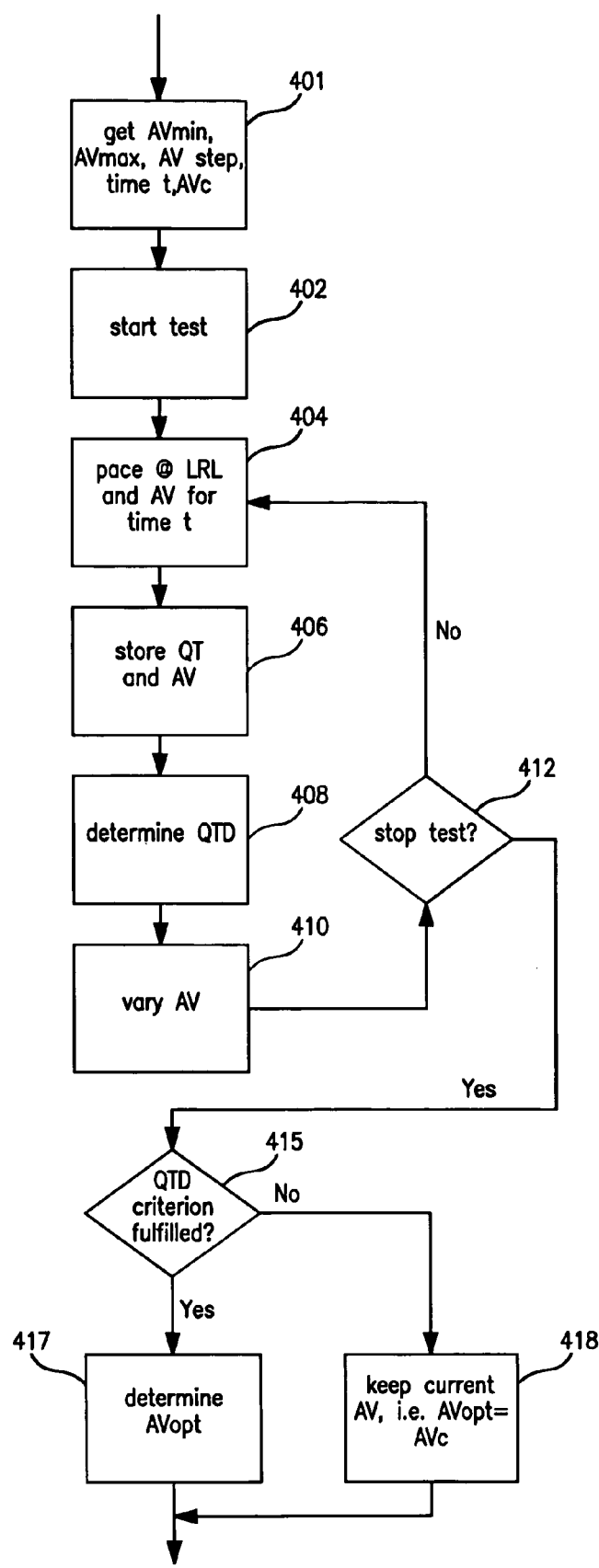
FIG. 8 is a flow diagram showing the primary steps in carrying out a first preferred embodiment of an AV test in accord with this invention.

FIG. 8 shows the main steps in carrying out the first preferred embodiment of this invention. As seen in FIG. 6B, in this method AV is maintained constant for a time t, during which time the device determines QTD=QT max−QT min. These difference figures, representing a measure of QT variation at each AV tested, are used to determine the optimal value of AV. AT 401 the device gets values of AV min, AV max, AV step, time t (in minutes or cycles) and AVc (current AV). AV min, AV max and AV step are used to program the different values of AV to be used. For example, the test can start with AV=AV min, and step up by 25 ms until the next value would exceed AV max. Note that during this sequence one of the AV values will be AVc, so that QTD will be measured for the current AV as well as other values. Time t is a programmable variable, but is suitably limited to about 1 minute. The test is initiated at 402, and at 404 pacing is commenced at LRL and the first value of AV for time t. At 406 QT values are determined and max and min values of QT are stored. After time t, QTD is determined at 408, and stored along with the corresponding value of AV. At 410 AV is varied, e.g., by increasing it by 25 ms. At 412 it is determined whether the test should continue by comparing the new value of AV with AV max. If the test can continue, the program loops back to 404, and the steps are carried out for the next duration t. Note that each time AV is varied there is no need to wait for QT stabilization, but rather the test proceeds directly to obtain the next QTD. When all programmed values of AV have been tested, the program goes to 415 and determines whether the QTD criterion has been filled. This step involves determining whether the smallest value of QTD is significantly different from the QTD at AVc. This can be determined, by example, by comparing the difference to a predetermined threshold. If the QTD criterion is fulfilled, AV corresponding to the minimum QTD is set equal to AVopt at block 417; if not, then current AVc is kept as illustrated at 418.

Figure 9:
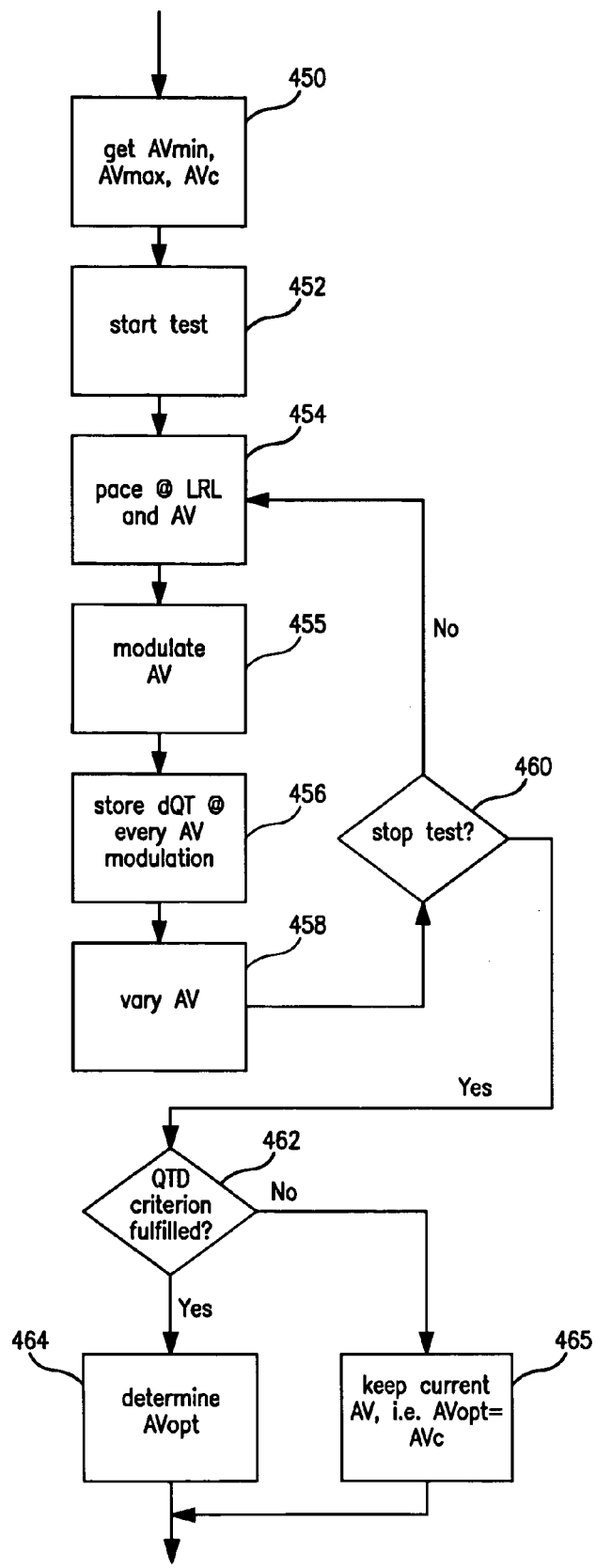
FIG. 9 is a flow diagram showing the primary steps in carrying out a second preferred embodiment of an AV test in accord with this invention.

The second preferred method of testing for QT variation in order to determine AVopt is illustrated by the flow diagram of FIG. 9. Assuming that test conditions have been met, at 450 the values of AVmin, AVmax and AVc are obtained from memory. The test is initiated at 452, and at 454 pacing commences at LRL and the first base value of AV. Modulation of AV is performed, as indicated at 455, and dQT is calculated and stored for each modulation sequence, as seen at 456. Steps 458, 460, 462, 464 and 465 correspond to steps 410, 412, 415, 417 and 418 of FIG. 8. AV is varied through the range of selected values, and dQT is stored for each base value. If the dQT criterion is fulfilled, meaning that the smallest dQT is significantly different from dQT from AVc, then a new value of AVopt is adopted for use; if not, AV remains as AVc.

The sequence of stepping the test through different values of AV is programmable. For example, the test can be started at a low value such as 75 ms and performed at intervals of 25 ms, i.e., 100 ms, 125 ms, etc. Alternately, the test sequence can start at AV=AVc, and if the differential is not significant the test can terminate without further evaluations at other settings of AV. Also, the test can be programmed to include smaller steps around AVc, e.g., steps of 5–10 ms.

The preceding specific embodiments are illustrative of the practice of the invention. It is to be understood, therefore, that other expedients known to those skilled in the art or disclosed herein, may be employed without departing from the invention or the scope of the appended claims. The present invention is not limited to any particular combination of hardware and software per se, but may find application with any form of software supplementing hardware.

The invention has been described with reference to the preferred embodiments, which embodiments use QT interval as the parameter that is monitored to obtain information from which AVopt is selected. However, other features or segments of the QRS-T wave that reflect changes in ventricular contractility due to the AV setting can be used within the scope of the invention. The algorithm used to obtain QT instability in response to different AV settings is a matter of choice. But in accord with this invention, the test can be carried out quickly and without any substantial delay after the initial wait for QT stabilization. For example, if the test is conducted at 12 different values of AV, and the data gathering period t for each AV step is less than one minute, then the entire test takes less than 12 minutes after the initialization. For a test where duration t is no longer than 10 seconds, the test would take only about 2 minutes. As discussed above, the test can be repeated, if desired, and a second rate somewhat above LRL, after which an AV(R) curve can be constructed, for providing AV values over a range of pacing rates. Also, the AV curve for use following an atrial sense (AS) can be constructed from the AV curve for pacing, in a known manner.

As used in this description of preferred embodiments and in the following claims, the term "optimal" is used in terms of the best that can be found, or determined. Thus, while it can't be said that an AV setting is absolutely optimal for the patient, non-the-less the invention sets an AVopt at LRL that is optimised in view of the analysis of QT data.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable cardiac pacing system capable of delivering atrial pace signals at a determined pacing rate and synchronously generating ventricular pace signals at a determined AV delay following delivery of atrial pacing signals and including an AV delay optimizing subsystem, said AV delay optimizing subsystem comprising:
   test means for initiating a test to determine an optimal AV delay corresponding to a pacing rate at about a lower rate limit (LRL);
   rate means for setting a cardiac pacing rate at or near the LRL;
   AV delay means for varying a AV delay interval value to each one of a plurality of respective AV values and for maintaining the AV delay interval value at each said respective AV value for a time t;
   QT means operative during the time t of each maintained AV delay value for measuring variation of QT over said time t and for determining a QT differential (QTD) over said time t; and
   optimizing means for determining the optimal AV delay, wherein said optimal AV delay corresponds to a minimal QTD, and for programming said optimal AV delay as an operating AV delay.

2. A system according to claim 1, wherein said QT means comprises means for determining QTmax and QTmin during each said time t and means for determining the difference between QTmax and Qtmin to provide said QTD.

3. A system according to claim 1, comprising timing means for setting said time t to a predetermined value less than about 10 seconds.

4. A system according to claim 1, comprising timing means for setting said time to a predetermined number of discrete cardiac cycles.

5. A system according to claim 1, wherein said AV delay means comprises increment means for setting said AV delay values to a predetermined low value (AVmin) plus an integer (n) multiplied by a difference in time ($\Delta T$), and program means for programming operating values of AVmin, n and $\Delta T$.

6. A system according to claim 1, wherein said AV means comprises program means for automatically cycling through each of said plurality of respective AV values.

7. A system according to claim 1, comprising evaluation means for evaluating the minimal value of QTD and for changing the AV delay to the value corresponding said minimal value if said minimal value differs significantly from QTD of the AV value prior to initiating said test.

8. A system according to claim 1, wherein said test means comprises storage means for a storing test criteria and monitoring means for determining that said test criteria are met before initiating a said test.

9. A system according to claim 8, wherein said storage means stores criteria for a pacing mode and a QT stability value.

10. A system according to claim 1, comprising AV(r) means for generating an AV(r) curve based on said optimized AV delay.

11. An implantable pacing system for pacing a patient's heart, having means for generating and delivering atrial pace signals at a determined pacing rate and means for generating ventricular pulses at a determined AV delay following an atrial pace event, and including an AV optimizing subsystem, said AV optimizing subsystem comprising:
    test means for initiating a test to determine an optimal AV delay corresponding to a pacing rate near a lower rate limit (LRL);
    rate means for setting pacing rate near the LRL;
    AV delay means for providing a set of respective base values of the AV delay;
    setting means for setting a base value of each of the set of respective base values of the AV delay to each respective one of said set of base values and maintaining said base value for a predetermined duration, the test comprising a duration for each of the set of base values;
    modulation means for modulating discrete delay intervals to a plurality of test AV delay values, wherein said plurality of test AV delay values are near each of the set of base values during each said duration;
    QT variation means operative during each said duration for determining a change in QT (dQT) during the performance of the modulating function by the modulation means for each of the set of base values;
    minimum means for determining the minimum dQT from a set of dQT values derived from the set of base values; and
    optimizing means for setting an optimal AV to the base AV value corresponding to said minimum dQT.

12. A system according to claim 11, wherein said modulation means comprises a programmable apparatus.

13. A system according to claim 12, wherein said modulation means comprises means for incrementally increasing and decreasing a test AV delay with respect to each of the set of the base values during each duration.

14. A system according to claim 12, wherein said modulation means comprises means for increasing AV delay in n predetermined discrete steps and for decreasing AV delay in n predetermined discrete steps, whereby the AV delay is increased and decreased with respect to the base AV delay during each said duration.

15. A system according to claim 14, wherein said modulation means comprises a programmable storage structure for holding the value of n and the value of said discrete steps, and n=1.

16. A system according to claim 15, where n equals at least 2.

17. A system according to claim 11, wherein said AV means comprises a set of m programmable base values.

18. A system according to claim 17, wherein said optimizing means comprises means for determining when said minimum dQT is significantly different from a prior dQT determined prior to said test, and for not altering a prior operating AV delay when the optimized AV delay it is not significantly different from the prior operating AV delay.

19. A system according to claim 18, comprising means for automatically repeating said test within a predetermined time following a determination that said minimum dQT is not significantly different.

20. A system according to claim 11, further comprising program means for programming said test to be completed in less than about ten minutes.

21. A system according to claim 11, comprising program means for programming each duration to be completed in less than about 10 cardiac cycles.

22. A system according to claim 11, comprising AV(r) means for generating an AV(r) curve that includes said optimal AV delay.

* * * * *